United States Patent
Uchigaki et al.

(10) Patent No.: US 7,470,400 B2
(45) Date of Patent: Dec. 30, 2008

(54) SENSOR CARTRIDGE, SENSOR FEEDER, AND MEASURING INSTRUMENT

(75) Inventors: Takatoshi Uchigaki, Kyoto (JP); Takao Fukuoka, Kyoto (JP); Yasuhide Kusaka, Kyoto (JP); Katsumi Hamamoto, Otsu (JP)

(73) Assignee: ARKRAY, Inc., Kyoto (JP)

( * ) Notice: Subject to any disclaimer, the term of this patent is extended or adjusted under 35 U.S.C. 154(b) by 1226 days.

(21) Appl. No.: 10/204,508

(22) PCT Filed: Feb. 22, 2001

(86) PCT No.: PCT/JP01/01325

§ 371 (c)(1),
(2), (4) Date: Aug. 20, 2002

(87) PCT Pub. No.: WO01/63272

PCT Pub. Date: Aug. 30, 2001

(65) Prior Publication Data

US 2003/0013992 A1  Jan. 16, 2003

(30) Foreign Application Priority Data

Feb. 23, 2000 (JP) .............................. 2000-045773

(51) Int. Cl.
*G01N 33/00* (2006.01)

(52) U.S. Cl. .............................. 422/63; 422/50; 422/55; 422/58; 422/99; 422/102; 422/104

(58) Field of Classification Search .................. 422/50, 422/55, 58, 99, 102, 104, 63
See application file for complete search history.

(56) References Cited

U.S. PATENT DOCUMENTS

| 5,266,179 | A | 11/1993 | Nankai |
| 5,489,414 | A | 2/1996 | Schreiber |
| 5,510,266 | A | 4/1996 | Bonner et al. |
| 5,632,410 | A | 5/1997 | Moulton |
| 5,645,798 | A | 7/1997 | Schreiber |
| 5,720,924 | A | 2/1998 | Eikmeier |
| 5,863,800 | A | 1/1999 | Eikmeier |

FOREIGN PATENT DOCUMENTS

| DE | 4427363 | 3/1995 |
| EP | 0732590 | 9/1996 |
| JP | 3-503082 | 7/1991 |
| JP | 4-357452 | 12/1992 |
| JP | 6-308115 | 11/1994 |
| JP | 8-285858 | 11/1996 |
| JP | 2001-33418 | 2/2001 |
| WO | 89/04474 | 5/1989 |

*Primary Examiner*—Sam P Siefke
(74) *Attorney, Agent, or Firm*—Hamre, Schumann, Mueller & Larson, P.C.

(57) ABSTRACT

A sensor cartridge (1) for use on a sensor feeder includes a cartridge body (10) and a mold (12). The cartridge body (10) has an upper surface (10a), a front (10c) extending continously from the upper surface, and a plurality of sensor-holding slots (11). Each of the sensor-holding slots (11) includes a first opening formed in the upper surface (10a) and a second opening formed in the front (10c) and communicating with the first opening. The mold (12) closes the first opening and second openings in case sensors are charged in the sensor-holding slots (11).

16 Claims, 13 Drawing Sheets

SENSOR CARTRIDGE, SENSOR FEEDER, AND MEASURING INSTRUMENT

TECHNICAL FIELD

The present invention relates to a sensor cartridge for accommodating a sensor for measuring the concentration of a particular substance contained in body fluid, such as glucose contained in blood. The present invention also relates to a sensor feeder used for taking out a sensor from such a sensor cartridge, and to a measuring instrument provided with such a sensor cartridge.

BACKGROUND ART

For diabetes treatment, the concentration of glucose contained in blood of a patient (hereinafter referred to as "blood glucose level") need be maintained in a normal range, and the management of the blood glucose level by the patient himself or herself is an important treatment. Particularly, for the treatment of insulin-dependent diabetes, the patient needs to inject insulin by himself or herself to maintain the blood glucose level in a normal range, so that the measurement of the blood glucose level is essential for the patient.

Portable blood glucose level measuring instruments which can be used by the patient himself or herself is already commercially available, an example of which is disclosed in JP-A-4-357452. Generally, a blood glucose level measuring instrument comprises an instrument body, and a disposable sensor (test piece) for use as mounted to the main body. The sensor is provided with an enzyme electrode including an electrode portion and a reacting portion contacting the electrode portion. When a predetermined portion of the sensor is brought into contact with blood as an analyte, part of the blood is introduced into the reacting portion by capillary action, causing an enzyme reaction or an electrochemical reaction. As a result, an anode current is generated at the electrode portion contacting the reacting portion. The anode current is converted to a blood glucose level at an arithmetic circuit provided in the main body and the computation result is displayed at the display portion.

When such a sensor having an enzyme electrode, or a so-called biosensor is exposed to the air for a long period of time, the reagent contained in the reacting portion is deteriorated due to its absorption of water in the air. In such a case, accurate measurement results cannot be obtained. Therefore, this kind of sensor is supplied to the patient in a hermetically sealed state by wrapping the sensor with aluminum laminated film for example. In this case, for measuring the blood glucose level, the patient needs to first break the laminated film by hand and then take out the sensor from the laminated film wrappings for mounting to the measuring instrument. These steps need be performed properly without touching the enzyme electrode portion or the analyte-contacting portion, which gives psychological stress to the patient. This is rather serious for children, the elderly, adults who recognize not to be clever with their hands, or visually-defected patients. Since this kind of measuring instrument is usually designed to perform proper measurement with as small amount of analyte as possible, there is a tendency to reduce the size of a sensor. Accordingly, the proper handling of a sensor becomes increasingly difficult for the patient.

As a manner of hermetically sealing the sensors, a plurality of sensors may be collectively sealed in a can provided with a lid for example, instead of individually wrapping each sensor with a laminated film as described above. According to this arrangement, for measuring the blood sugar level, the patient needs to open the lid of the can to take out one sensor for mounting to the measuring instrument. This causes a problem that all the sensors in the can are exposed to the air every time the lid is opened. Further, this arrangement does not considerably facilitate the handling of the sensors as compared with the manner of wrapping the sensors with laminate films. Thus, the handling of the sensors become difficult as the sensors become smaller in size.

JP-A-6-308115 discloses another manner of hermetically sealing the sensors, which utilizes a cartridge. The cartridge includes a plurality of chambers arranged in a row, each of which accommodates a sensor. Specifically, each chamber of the cartridge has a cylindrical configuration which is open at opposite ends thereof. The sensor cartridge is mounted to a predetermined sensor feeder provided with a projecting bar. By inserting the projecting bar into each of the chambers through one end toward the other end thereof, the sensor is pushed out from the chamber through the other end.

With this arrangement, the handling of the sensors is easier than in the above-described arrangements, because the user, or the patient need not manually peel off the sealing member at each chamber of the sensor cartridge. However, it still has the following problems.

Firstly, since the sensor pushed by the projecting bar needs to break through the sealing member sealing the end of the chamber, the materials for the sensors are limited to certain kinds in view of the rigidity. This may hinder the size reduction and thickness reduction of the sensors.

Secondly, the manufacturing of the sensor cartridge is troublesome, because it is required to insert sensors in respective chambers and to separately seal opposite ends of each chamber with a sealing member.

DISCLOSURE OF THE INVENTION

It is an object of the present invention to eliminate or lessen the problems described above. Specifically, an object of the present invention is to provide a sensor cartridge which enables taking-out of the hermetically-sealed sensors by a simple operation and which can be manufactured easily. Another object of the present invention is to provide a sensor feeder provided with such a sensor cartridge, and a measuring instrument provided with such a sensor cartridge.

According to a first aspect of the present invention, there is provided a sensor cartridge used as attached to a main body of a sensor feeder. The cartridge includes a cartridge body and a sealing member. The cartridge body includes an upper surface, a front surface connected thereto, and a plurality of sensor retaining grooves. Each of the sensor retaining grooves includes a first opening formed at the upper surface and a second opening formed at the front surface for communication with the first opening. The sealing member closes the first opening and the second opening with a sensor loaded in the sensor retaining groove.

Preferably, the sensor retaining groove includes a sensor accommodating portion for accommodating the sensor, and a pusher receiving portion for receiving a pusher contained in the main body of the sensor feeder. The sensor accommodating portion communicates with the first opening and the second opening. The pusher receiving portion communicates with the first opening while being connected to the sensor receiving portion at a location opposite to the second opening.

Preferably, the sensor retaining groove includes a sensor accommodating portion for accommodating the sensor, and a cutter receiving portion for receiving a cutter contained in the main body of the sensor feeder. The sensor accommodating portion and the cutter receiving portion communicate with the first opening and the second opening while being connected to each other.

Preferably, the cutter receiving portion is deeper than the sensor accommodating portion in a thickness direction of the sensor cartridge.

Preferably, the front surface is connected to the upper surface via a rounded portion.

Preferably, the cartridge further includes a rear surface opposing the front surface, and the rear surface is formed with feed grooves for engaging a pin contained in the main body of the sensor feeder and for advancing the sensor cartridge by a predetermined pitch in response to one reciprocal movement of the pin.

Preferably, each of the feed grooves includes a first groove portion extending thicknesswise of the sensor cartridge and a second groove portion extending between an intermediate portion of the first groove portion and an upper end of an adjacent first groove portion.

Preferably, the intermediate portion of the first groove portion is provided with a projection for guiding the pin moving upward within the first groove portion toward the second groove portion.

Preferably, the second groove portion is provided with a projection for preventing the pin from entering the second groove portion from the upper end of the first groove portion.

Preferably, the plurality of sensor retaining grooves are arranged at the predetermined pitch.

According to a second aspect of the present invention, there is provided a sensor feeder comprising a sensor cartridge and a pusher. The sensor cartridge includes a cartridge body and a sealing member for accommodating a plurality of sensors. The pusher is movable vertically and back and forth for pushing one of the plurality of sensors. The cartridge body includes an upper surface, a front surface connected thereto, and a plurality of sensor retaining grooves. Each of the sensor retaining grooves includes a first opening formed at the upper surface and a second opening formed at the front surface for communication with the first opening. The sealing member closes the first opening and the second opening with a sensor loaded in the sensor retaining groove. The sensor retaining groove includes a sensor accommodating portion for accommodating the sensor, and a pusher receiving portion for receiving the pusher. The sensor accommodating portion communicates with the first opening and the second opening, and the pusher receiving portion communicates with the first opening while being connected to the sensor receiving portion at a location opposing the second opening.

Preferably, the feeder further includes a cutter for breaking the sealing member. The sensor retaining groove includes a cutter receiving portion for receiving the cutter. The cutter receiving portion communicates with the first opening and the second opening while being connected to the sensor accommodating portion.

Preferably, the feeder further includes a pin, and the cartridge body includes a rear surface opposite to the front surface. The rear surface is formed with feed grooves for engaging the pin and for advancing the sensor cartridge by a predetermined pitch in response to one reciprocal movement of the pin.

Preferably, the feeder further includes an operation member which is movable vertically and back and forth. The pusher, the cutter and the pin are movable vertically in response to the vertical movement of the operation member. The pusher is movable back and forth in response to the back-and-forth movement of the operation member.

Preferably, the feeder further includes a spring for biasing the operation member upward.

According to a third aspect of the present invention, there is provided a measuring instrument. The measuring instrument comprises a plurality of sensors each of which includes an analyte applying portion, a reacting portion, and a base end provided with a sensor terminal, a sensor cartridge including a cartridge body and a sealing member for accommodating the plurality of sensors, a pusher movable vertically and back and forth for pushing one of the plurality of sensors, and an arithmetic circuit including a circuit terminal for performing computation based on a current generated at the reacting portion. The cartridge body includes an upper surface, a front surface connected thereto, and a plurality of sensor retaining grooves. Each of the sensor retaining grooves includes a first opening formed at the upper surface and a second opening formed at the front surface for communication with the first opening. The sealing member closes the first opening and the second opening with the sensor loaded in the sensor retaining groove. The sensor retaining groove includes a sensor accommodating portion for accommodating the sensor, and a pusher receiving portion for receiving the pusher. The sensor accommodating portion communicates with the first opening and the second opening. The pusher receiving portion communicates with the first opening while being connected to the sensor receiving portion at a location opposite the second opening. The sensor is accommodated in the sensor accommodating portion so that the analyte applying portion faces the second opening. The circuit terminal is so provided as to contact the sensor terminal of the sensor when the analyte applying portion is pushed by the pusher for exposure to the outside of the instrument.

Preferably, the instrument further includes a cutter for breaking the sealing member, and the sensor retaining groove includes a cutter receiving portion for receiving the cutter. The cutter receiving portion communicates with the first opening and the second opening while being connected to the sensor accommodating portion.

Preferably, the instrument further includes a pin, and the cartridge body includes a rear surface opposing the front surface. The rear surface is formed with feed grooves for engaging the pin and for advancing the sensor cartridge by a predetermined pitch in response to one reciprocal movement of the pin.

Preferably, the instrument further includes an operation member which is movable vertically and back and forth, and a movable member which is movable vertically together with the operation member. The pin is provided at the movable member.

According to a fourth aspect of the present invention, there is provided a sensor cartridge. The sensor cartridge comprises a cartridge body having an upper surface and a plurality of sensor retaining grooves each having an opening formed at the upper surface, and a sealing member for closing the opening. Each of the sensor retaining grooves includes a sensor accommodating portion for accommodating the sensor, and a cutter receiving portion for receiving a cutter for breaking the sealing member. The sensor accommodating portion and the cutter receiving portion communicate with the opening while being connected to each other.

Other features and advantages of the present invention will become clearer from the detailed description given below with reference to the accompanying drawings.

MODE FOR CARRYING OUT THE INVENTION

Figure 1:
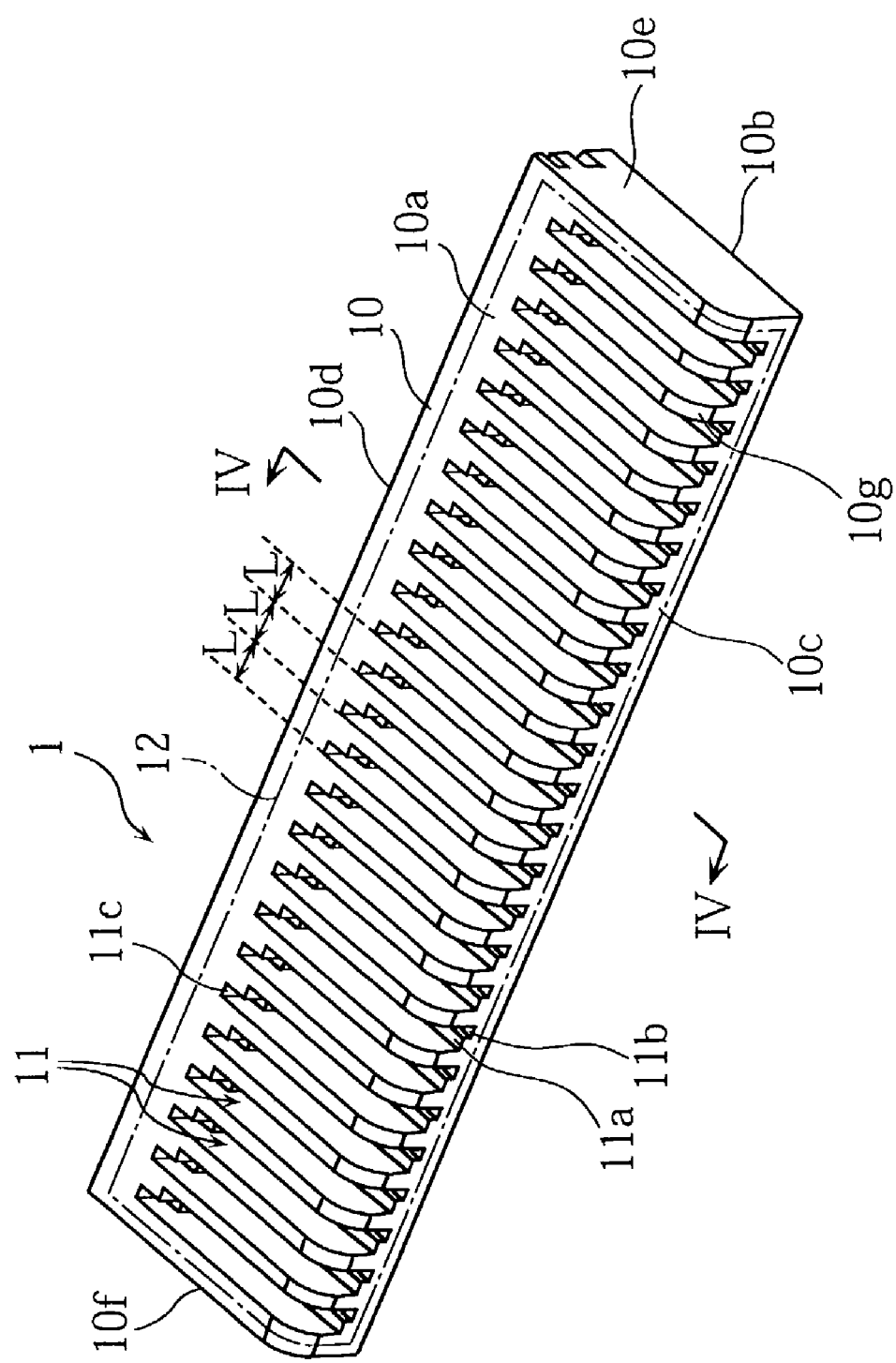
FIG. 1 is a perspective view illustrating an example of sensor cartridge according to the present invention.

Preferred embodiments of the present invention will be described below with reference to the accompanying drawings.

FIGS. 1-4 illustrates an example of sensor cartridge according to a first aspect of the present invention. The sensor cartridge includes a cartridge body 10 and a sealing member 12.

The cartridge body 10 is molded from a moisture-impermeable resin such as high-density polyethylene to have a general contour of an elongate parallelepiped. Specifically, the contour of the cartridge body 10 is defined by an upper surface 10a, a bottom surface 10b, a front surface 10c, a rear surface 10d and end surfaces 10e, 10f. The upper surface 10a, the front surface 10c and the end surface 10e are generally parallel to the bottom surface lob, the rear surface 10d and the end surface 10f, respectively. The upper surface 10a is connected to the front surface 10c via a rounded portion 10g. Hereinafter, the direction extending from the upper surface 10a toward the bottom surface 10b is defined as the thickness direction of the sensor cartridge 1 or the cartridge body 10. Similarly, the direction extending from the front surface 10c toward the rear surface 10d is defined as the widthwise direction, whereas the direction extending from the end surface 10e toward the end surface 10f is defined as the longitudinal direction of the sensor cartridge 1 or the cartridge body 10.

Figure 2:
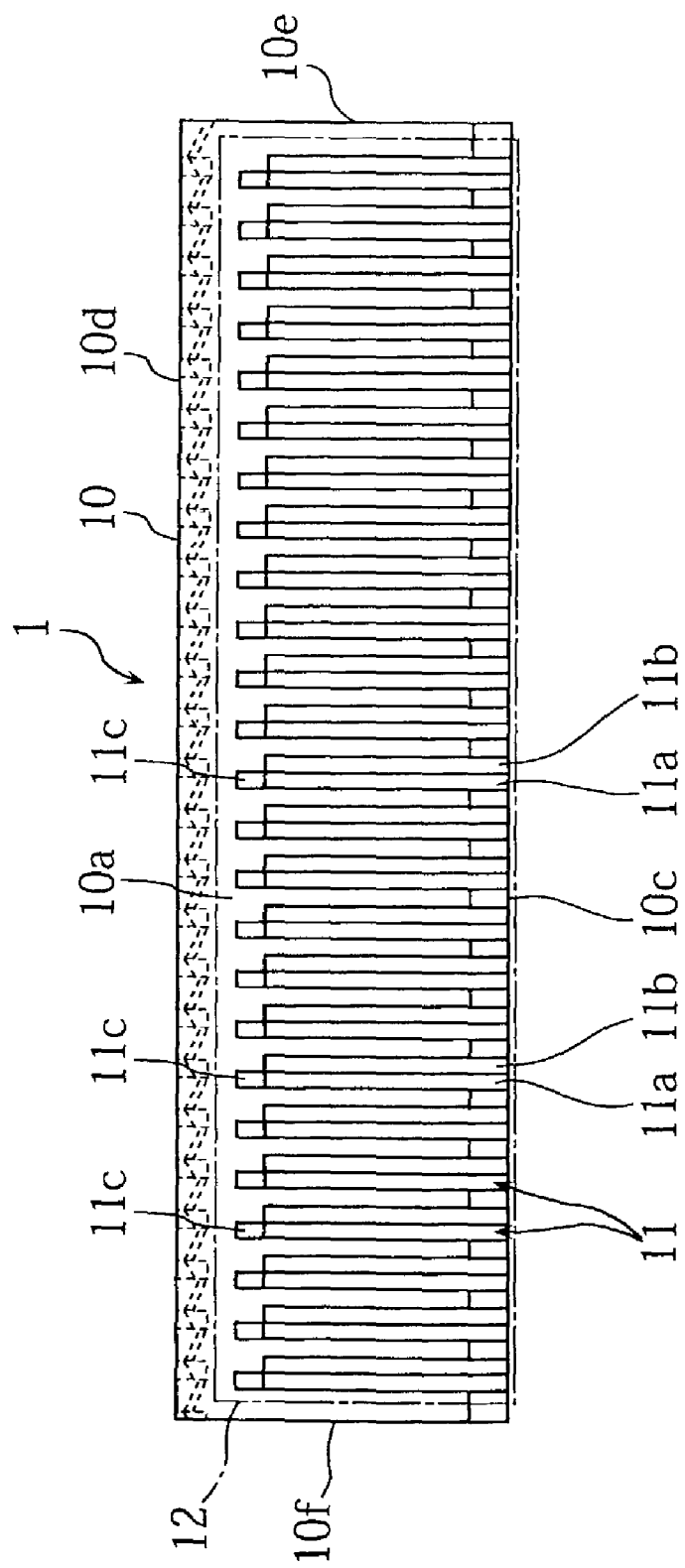
FIG. 2 is a plan view of the sensor cartridge shown in FIG. 1.

The cartridge body 10 is formed with a plurality of sensor retaining grooves 11 which are arranged at a predetermined pitch L longitudinally of the sensor cartridge and extend widthwise. Each of the sensor retaining grooves 11 is open at the upper surface 10a, the rounded portion 10g and the front surface 10c. As shown in FIGS. 1 and 2, each sensor retaining groove 11 comprises a sensor accommodating portion 11a for directly accommodating a sensor 2, a cutter receiving portion 11b and a pusher receiving portion 11c for respectively receiving a cutter and a pusher included in a sensor feeder. The dimension of the sensor accommodating portion 11a is determined correspondingly to that of the sensor 2 to be received therein. The cutter receiving portion 11b is located adjacent to the sensor accommodating portion 11a for communication therewith and is open, together with the sensor accommodating portion 11a, at the upper surface 10a, the rounded portion 10g and the front surface 10c of the cartridge body 10. The cutter receiving portion 11b is deeper than the sensor accommodating portion 11a in the thickness direction. The pusher receiving portion 11c, which is open at the upper surface 10a, is arranged adjacent to and in communication with an end of the sensor accommodating portion 11a extending widthwise. The pusher receiving portion 11c is substantially equal in width to the sensor accommodating portion 11a but shallower than the sensor accommodating portion 11a in the thickness direction.

Figure 4:
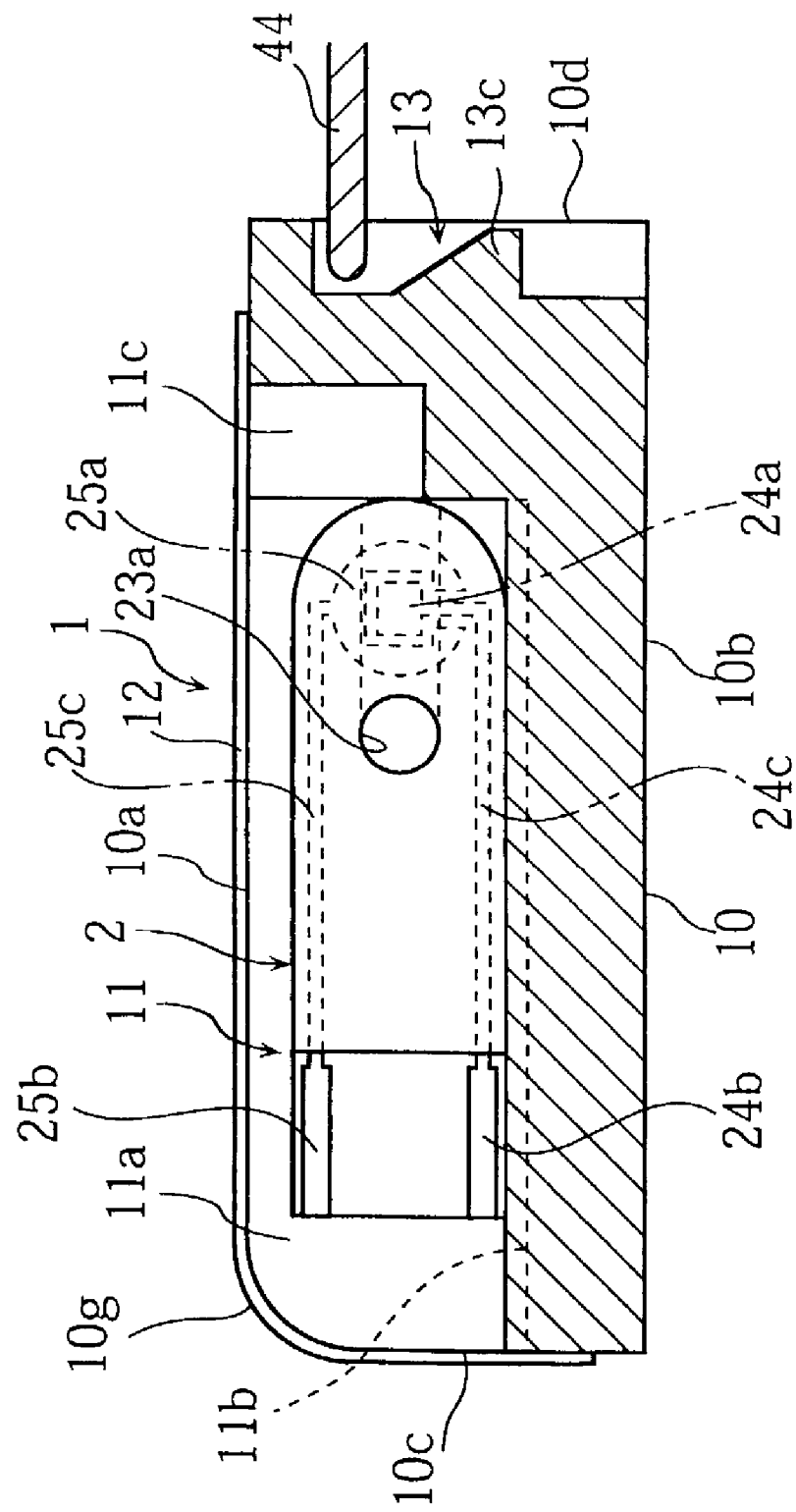
FIG. 4 is a sectional view taken along lines IV-IV in FIG. 1.

As shown in FIG. 4, a sensor 2 in the form of a short sheet strip is loaded in each of the sensor retaining grooves 11. The sheet-like sealing member 12 is provided to continuously extend over the upper surface 10a, the rounded portion 10g and the front surface 10c of the cartridge body 10 to collectively close the openings of all the sensor retaining grooves 11. Thus, each of the sensor retaining grooves 11 is hermetically sealed. For the sheet-like sealing member 12, use may be made of aluminum foil or a laminated member formed by laminating a resin film on an aluminum foil.

Figure 3:
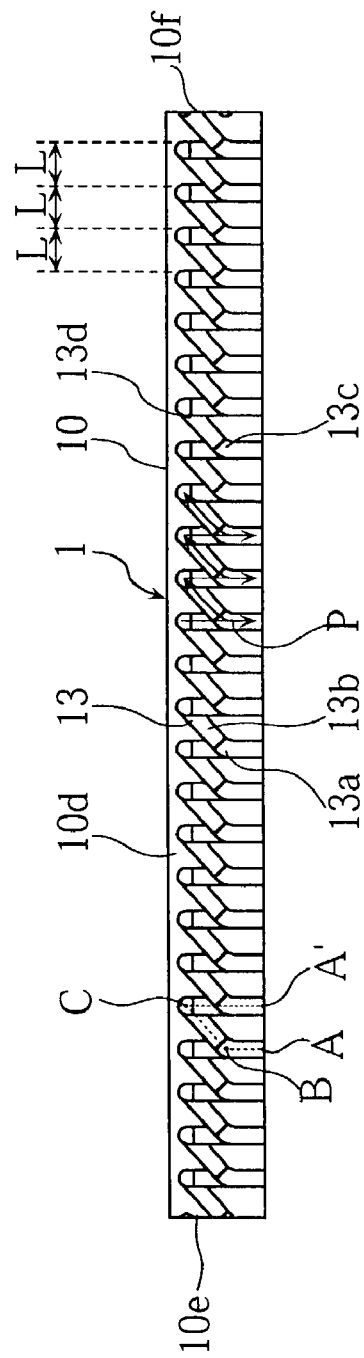
FIG. 3 is a rear view of the sensor cartridge shown in FIG. 1.

As shown in FIG. 3, the rear surface 10d of the cartridge body 10 is formed with feed grooves 13. The feed grooves 13 receive a pin-like driver which is included in the sensor feeder to be described later and which is movable reciprocally thicknesswise of the sensor cartridge 1, thereby providing a cartridge feed mechanism in the sensor feeder together with the pin-like driver. Each of the feed grooves 13 includes a first groove portion 13a extending thicknesswise of the sensor cartridge 1 and a second groove portion 13b extending between an intermediate portion of the first groove portion 13a and the upper end of an adjacent first groove portion 13a. The first groove portions 13a are arranged at a predetermined pitch L longitudinally of the sensor cartridge 1. Each feed groove 13 is formed, at the bottom thereof, with projections 13c, 13d so that the pin-like driver, which is movable reciprocally in the sensor feeder thicknesswise of the sensor cartridge 1, properly moves within the feed grooves 13 along the path indicated by the arrow P.

Figure 3A:
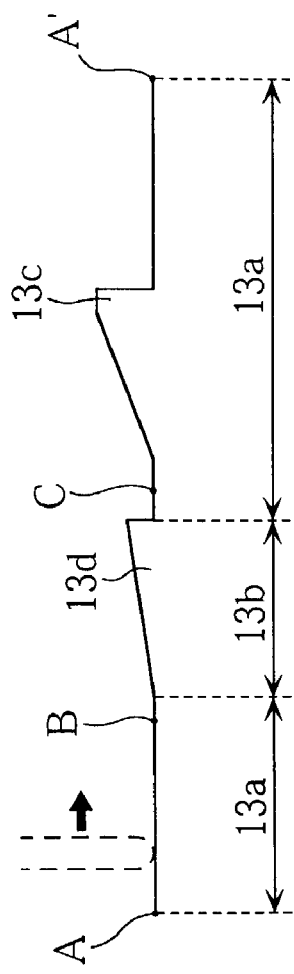

FIG. 3a illustrates undulations along the pin transfer path in the feed grooves 13. The points A, B, C, A' in FIG. 3a correspond to the points A, B, C, A' at the surfaces of the feed grooves 13 shown in FIG. 3. When the pin-like driver indicated by broken lines in FIG. 3a moves upward from the point A within the first groove portion 13a, the pin-like driver comes into contact with the projection 13c adjacent to the point B and is guided into the second groove portion 13b. Then, the pin-like driver moves over the projection 13d at the bottom surface of the second groove portion 13b to reach the point C, which generally corresponds to the upper end of the next first groove portion 13a. The movement of the pin-like driver which has reached the point C is restricted by the projection 13d so as not to move back along the second groove portion 13b. The pin-like driver then moves downward from the point C to pass over the projection 13c to reach the point A'.

In this way, during a single reciprocal movement of the pin-like driver thicknesswise of the sensor cartridge 1, the pin-like driver of the sensor feeder moves from one first groove portion 13a to be received in the adjacent first groove portion 13a. Since the first groove portions 13a are arranged at the predetermined pitch L, the reciprocal movement of the pin-like driver advances the sensor cartridge 1 stepwise at the pitch L longitudinally thereof relative to the pin-like driver or the main body of the sensor feeder.

The sensor cartridge 1 having the above-described structure has the following advantages. Since each of the sensor retaining grooves 11 is open at the upper surface 10a of the cartridge body 10, a sensor can be easily inserted therein from above. Further, since both the upper opening and the front opening of each sensor retaining groove 11 are sealed by the sheet-like sealing member, the interior of the sensor retaining groove can be easily maintained in a hermetically sealed state. Moreover, since the upper surface 10a and the front surface 10c of the cartridge body 10, to which the sealing member is to be attached, are connected to each other via the rounded portion 10g of the cartridge body 10, all the sensor retaining grooves 11 can be sealed by a single sheet of sealing member by a single, relatively easy process step. Therefore, the sensor cartridge 1 can be made by a manufacturing process which is relatively easy in terms of the loading of sensors and the sealing with a sealing member, which enhances the manufacturing efficiency.

Figure 5:
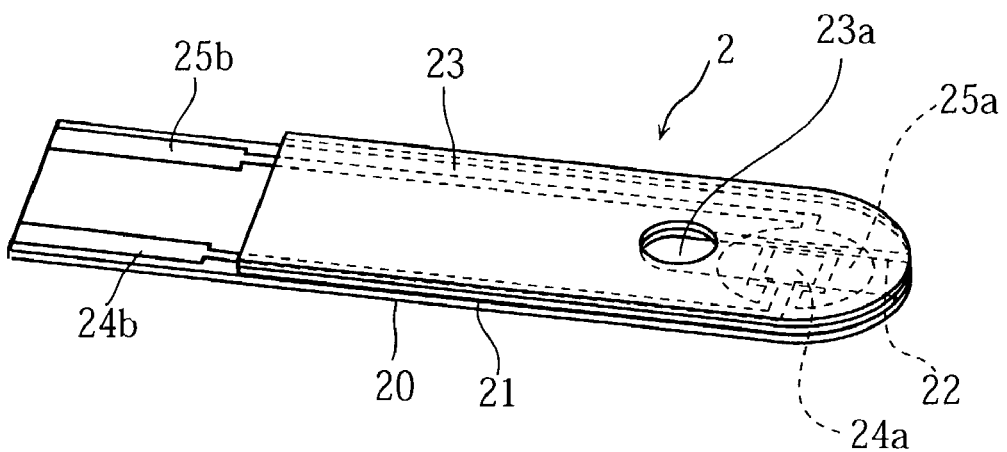
FIG. 5 is a perspective view showing an example of sensor for accommodation in a sensor cartridge of the present invention.
Figure 6:
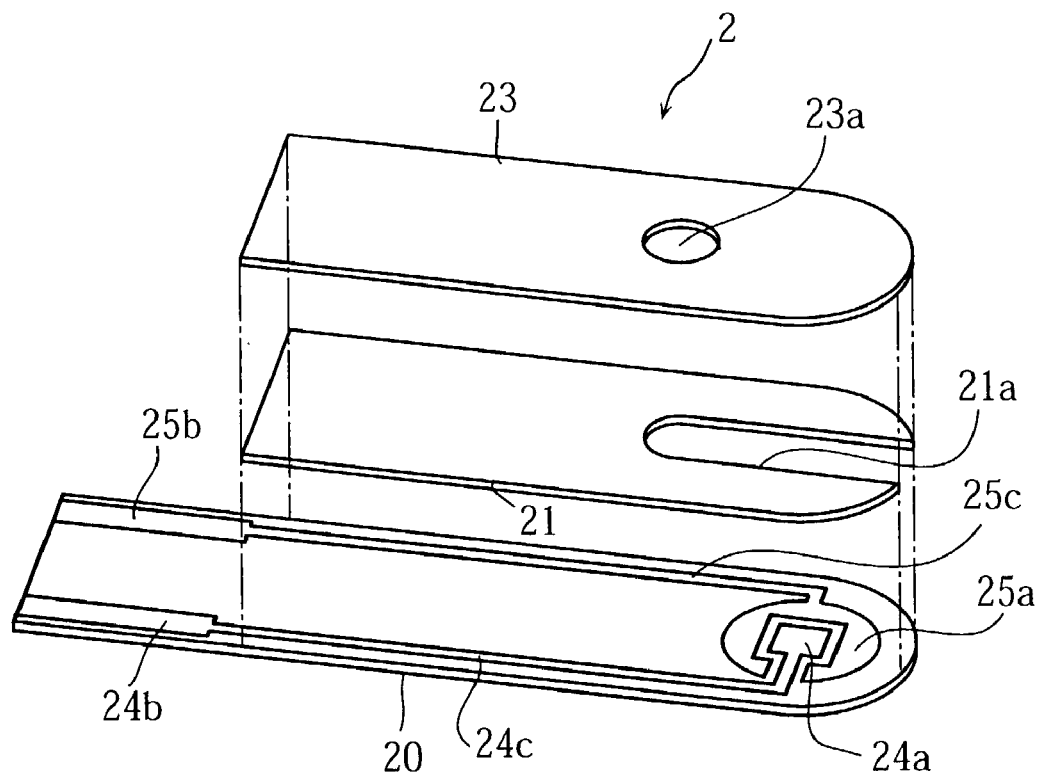
FIG. 6 is an exploded perspective view of the sensor shown in FIG. 5.

FIGS. 5 and 6 illustrate an example of biosensor 2 to be accommodated in the above-described sensor cartridge 1. The biosensor 2, which is in the form of a short sheet strip having a rounded tip end, includes an insulating base 20, a spacer plate 21 laminated on the base 20, and a cover plate 23 further laminated on the spacer plate 21. The insulating base 20 is formed with an operative electrode pattern 24 and a counterpart electrode pattern 25.

The operative electrode pattern 24 is made up of a rectangular operative electrode 24a provided adjacent the tip end of the insulating base 20, a terminal 24b provided adjacent the base end of the insulating base 20, and a lead 24c connecting these to each other. The counterpart electrode pattern 25 is made up of a counterpart electrode 25a surrounding the operative electrode 24a adjacent the tip end of the insulating base 20, a terminal 25b provided adjacent the base end of the insulating base 20, and a lead 25c connecting these to each other.

The spacer plate 21, which has a tip end configured identically to that of the insulating base 20, is shorter than the insulating base 20. Therefore, in the state where the spacer plate 21 is laminated on the insulating base 20, the terminals 24b, 25b provided adjacent the base end of the insulating base 20 are exposed to the outside. The spacer plate 21 is formed with a slit 21a open at the tip end of the sensor. The spacer 21 is laminated on the insulating base 20 so that the operative electrode 24a and the counterpart electrode 25a are exposed at the slit 21a. The portions formed with the operative electrode 24a and the counterpart electrode 25a are provided with a non-illustrated reagent layer, or a reacting portion.

The cover plate 23, which has a rounded tip end similarly to the insulating base 20, is formed with a through-hole 23a which communicates with the base end of the slit 21a of the spacer plate 21. Thus, a body fluid path 22 is defined by the slit 21a of the spacer plate 21, and the cover plate 23 and the insulating base 20 sandwiching the spacer plate 21 from above and below. The body fluid path 22 is open at one end adjacent the tip end of the sensor while also being open at the other end via the through-hole 23a formed in the cover plate 23.

In the case where the sensor 2 is used for measuring the blood glucose level, the reacting portion contains a reagent such as glucose oxidase which is an oxidization enzyme, and pottasium ferricyanide as a mediator. When the biosensor is loaded in a measuring instrument, the terminals 24b, 25b are electrically connected to the counterpart terminals of the instrument to be ready for measurement. When body fluid as an analyte is applied to the tip end of the sensor 2, the body fluid is introduced into the body fluid path 22 by capillary action. In the body fluid path, enzyme reaction and electrochemical reaction occur at the reacting portion which is made up of the operative electrode 24a, the counterpart electrode 25a and the reagent layer covering these electrode, thereby generating anode current at the operative electrode. It is to be noted that the sensor 2 is not limited to the above-described biosensor in the form of a short sheet strip, and use may be made of any other sensor as long as it includes an analyte applying portion and terminals while having a configuration suitable for insertion into a measuring instrument.

Figure 7:
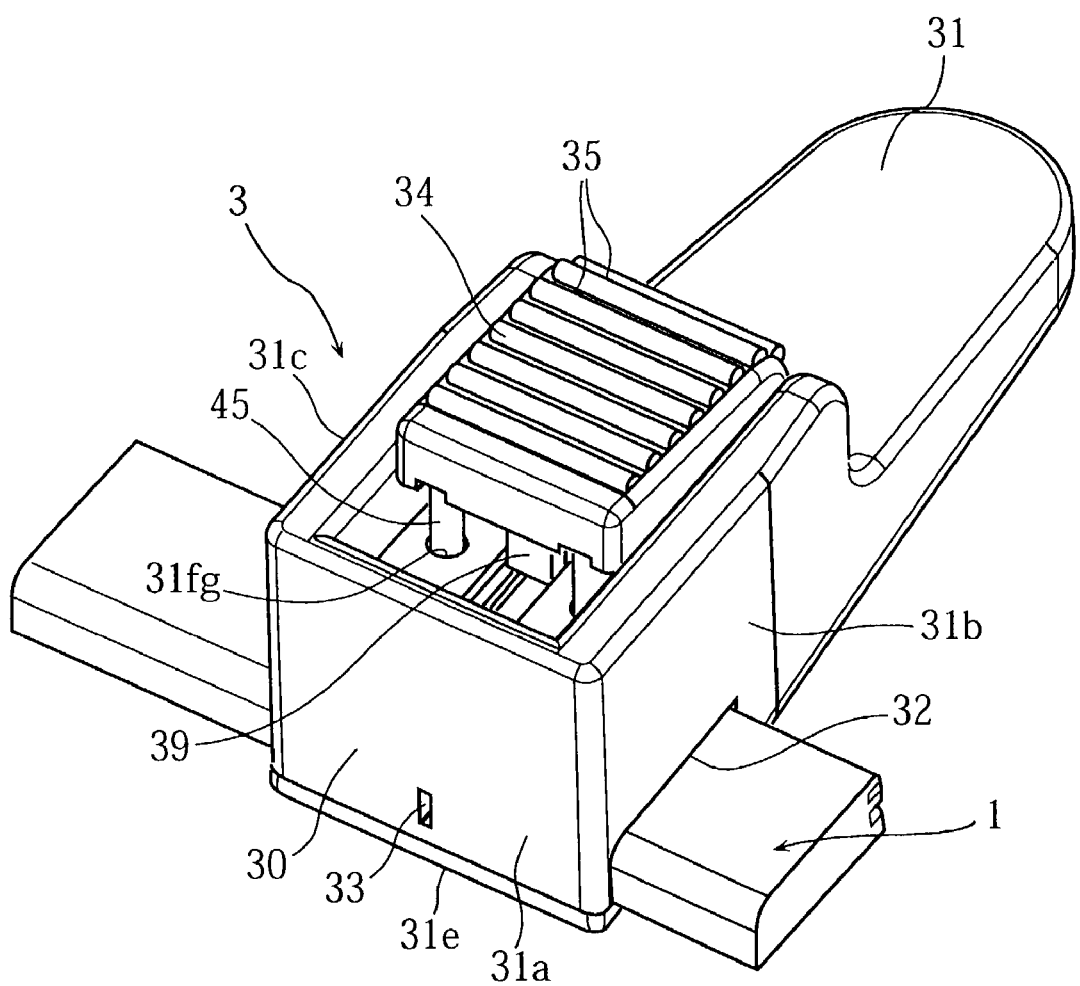
FIG. 7 is a perspective view showing an example of sensor feeder according to the present invention.
Figure 8:
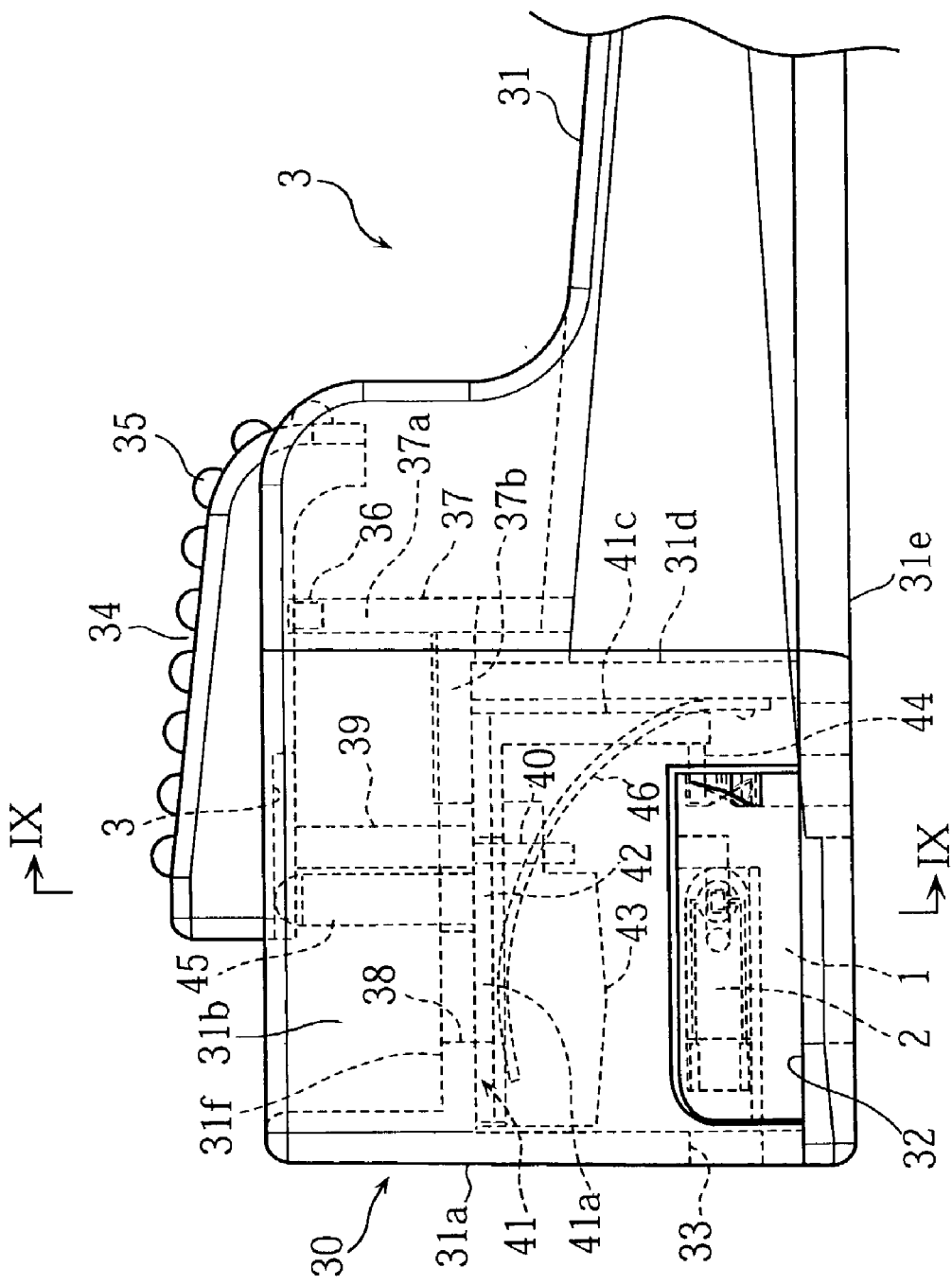
FIG. 8 is a side view of the sensor feeder shown in FIG. 7.

FIGS. 7-12 illustrate a sensor feeder 3 according to a second aspect of the present invention. As shown in FIG. 7, the sensor feeder 3 includes a cartridge mount portion 30, a grip portion 31 extending from the cartridge mount portion 30, and an operation member 34 supported by the cartridge, mount portion 30. In this feeder, the side provided with the cartridge mount portion 30 is regarded as the front, whereas the side provided with the grip portion 31 is regarded as the rear.

The cartridge mount portion 30 is in the form of an upwardly-open box defined by a front wall 31a, a side wall 31b, an opposite side wall 31c, a vertical partition wall 31d adjoining the grip portion 31 and a bottom wall 31e. The cartridge mount portion 30 is formed with a sensor cartridge insertion hole 32 penetrating through the side walls 31b, 31c. The front wall 31a is formed with a sensor eject hole 33.

The operation member 34 is movable vertically and back and forth relative to the cartridge mount portion 30. Specifically, as shown in FIGS. 8-12, the cartridge mount portion 30 is upwardly provided with an upwardly-open accommodation recess defined by the front wall 31a, the side walls 31b, 31c and a horizontal partition wall 31f. The operation member 34 is accommodated and retained in the accommodation recess. The operation member 34 has a width corresponding to the distance between the side walls 31b and 31c and has an upper surface formed with a plurality of non-slip projections 35. The operation member 34 is formed, at the sides thereof, with a guide projection 36. The guide projection 36 is slidable along a respective one of L-shaped guide grooves 37 formed on the inner surfaces of the side walls 31b and 31c. Each L-shaped guide groove 37 includes a vertically extending first portion 37a, and a second portion 37b extending horizontally from the lower end of the first portion. Thus, the operation member 34 is movable vertically along the first portion 37a of the guide groove 37 between a restored level and a pushed level. Further, at the pushed level, the operation member is movable horizontally along the second portion 37b between a retreated position and an advanced position. Herein, the restored level means the state where the guide projection 36 is located at the upper end of the first portion 37a of the guide groove 37, whereas the pushed level means the state where the guide projection 36 is located at the lower end of the first portion 37a or at any position within the second portion 37b. The retreated position means the state where the guide projection 36 is located at the connecting point between the first portion 37a and the second portion 37b, whereas the advanced position means the state where the guide projection 36 is located at the front end of the second portion 37b.

The operation member 34 has a lower surface which is integrally formed with a stay 39 extending downward through a horizontally-extending slit 38 formed at the horizontal partition wall 31f. The stay 39 has a lower end on which is integrally supported a plate-like pusher 40 capable of entering the pusher receiving portion 11c of each sensor retaining groove 11. Thus, the pusher 40 is movable back and forth correspondingly to the back-and-forth movement of the operation member 34. The operation member 34 is movable vertically along the first portion 37a of the guide groove 37 only at the retreated position. The stay 39 and the pusher 40 are so arranged that the pusher properly enters the pusher receiving portion 11c provided on the rear side of the sensor retaining groove 11 of the sensor cartridge 1 when the operation member 34 moves vertically at the retreated position.

The cartridge mount portion 30 incorporates, under the horizontal partition wall 31f, a movable member 41 which is movable vertically correspondingly to the vertical movement of the operation member 34. The movable member 41 includes a horizontal plate portion 41a and a rear skirt portion 41c extending downward from a rear portion of the horizontal plate portion 41a. Similarly to the horizontal partition wall 31f, the horizontal plate portion 41a is formed with a slit 42 for allowing the passage of the pusher 40 integrally provided under the operation member 34 for back-and-forth movement. The horizontal plate portion 41a of the movable member 41 is provided, at the lower surface thereof, with a cutter 43 extending downward. The cutter 43 is in the form of a plate capable of entering the cutter receiving portion 11b of the sensor retaining groove 11 of the sensor cartridge 1. The pin-like driver 44 for engagement with the feed grooves 24 formed at the rear surface 10d of the sensor cartridge 1 is provided at the skirt portion 41c of the movable member 41 to project forwardly. The skirt portion 41c provided with the driver 44 is elastically deformable to some extent under an external force. Therefore, when the pin-like driver 44 moves over the projections 13c, 13d of the feed grooves 13 as described with reference to FIG. 4, the skirt portion 41c elastically retreats.

Figure 9:
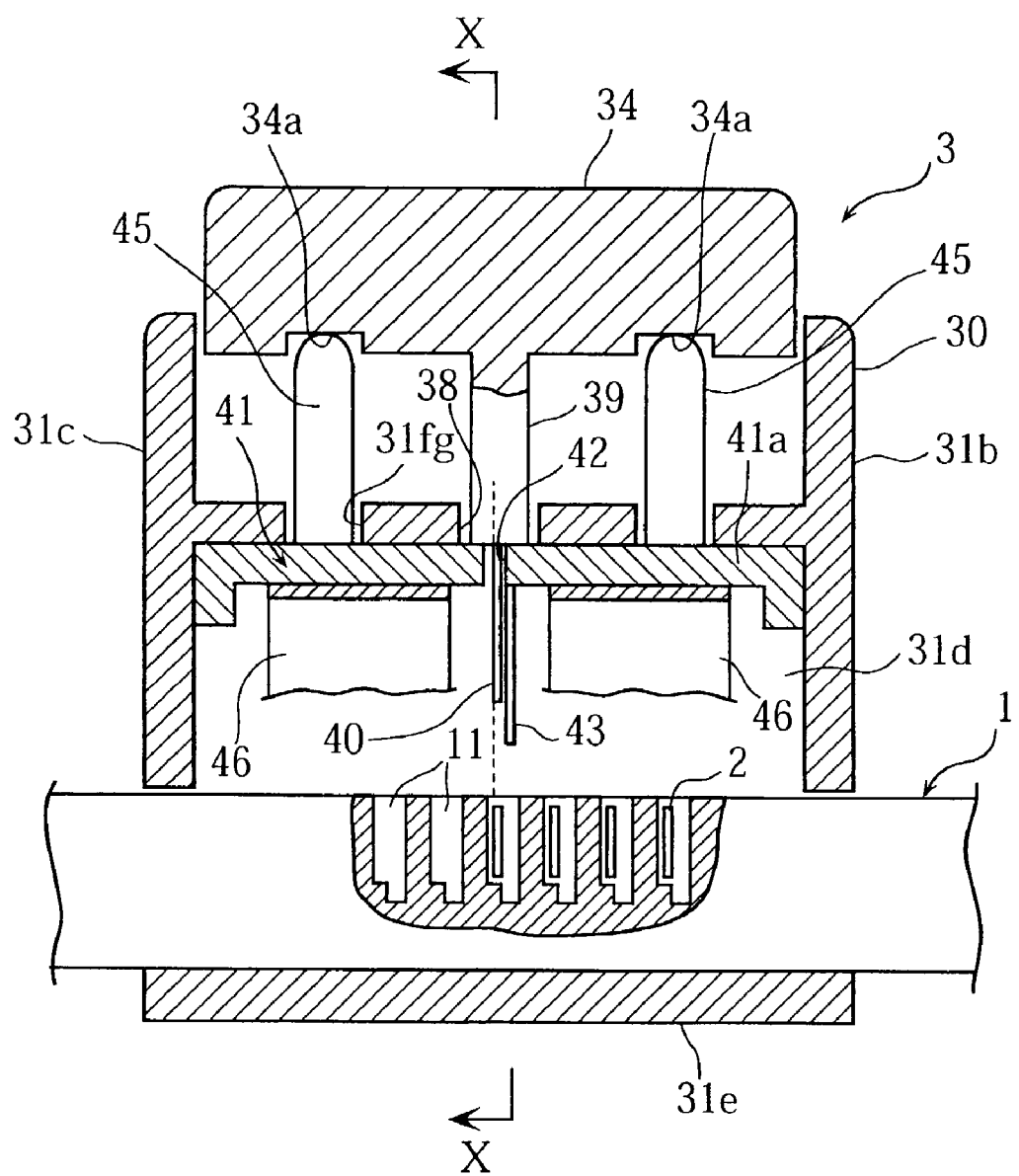
FIG. 9 is a sectional view taken along lines IX-IX of FIG. 8, showing the operation member held at the restored level.

As clearly shown in FIG. 9, a pair of upwardly-extending support bars 45 are integrally formed on the upper surface of the horizontal plate portion 41a of the movable member 41. Each support bar 45 penetrates through a guide hole 31fg formed in the horizontal partition wall 31f for engagement with the reverse surface of the operation member 34. The reverse surface of the operation member 34 is formed with guide grooves 34a each capable of sliding while receiving the upper end of the support bar 45.

Figure 10:
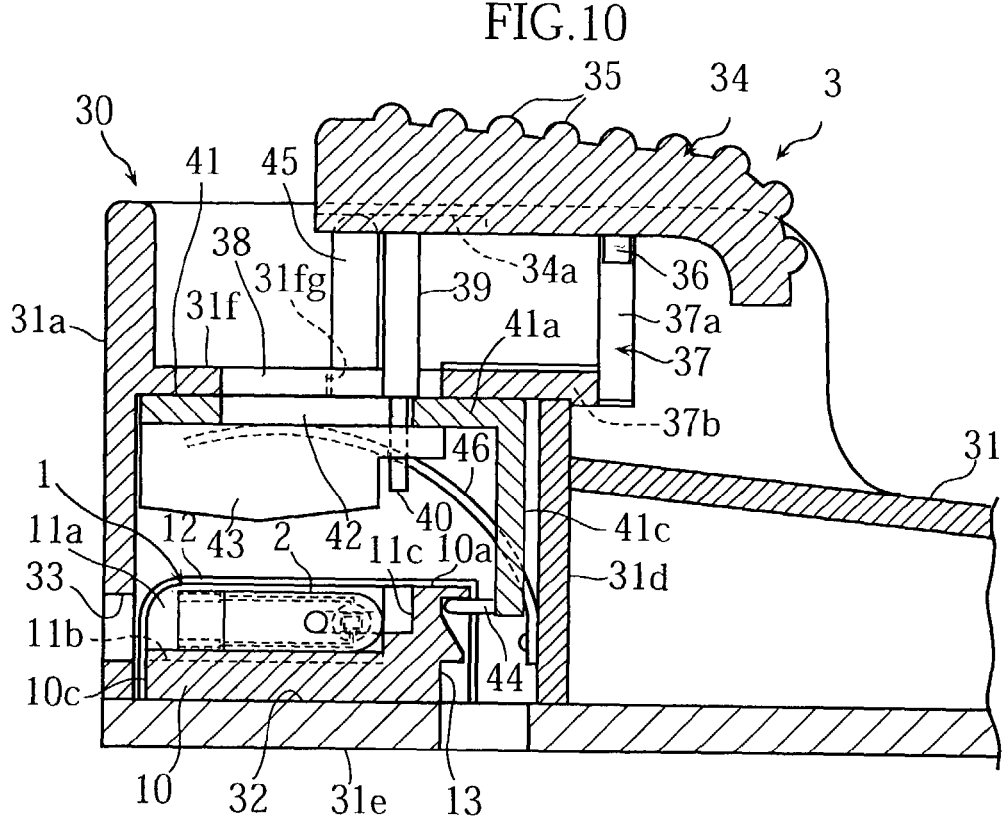
FIG. 10 is a sectional view taken along lines X-X of FIG. 9, showing the operation member held at the restored level.

As clearly shown in FIG. 10, a pair of leaf springs 46 are provided as elastically deformed, each of which has one end fixed to the vertical partition wall 31d with the other end engaging the lower surface of the horizontal plate portion 41a of the movable member 41. Thus, the movable member 41 is normally biased upwardly in the apparatus. Therefore, as long as the guide projection 36 engages the first portion 37a of each L-shaped guide groove 37, the operation member 34 is pushed by the movable member 41 for elastically restoring upward. A downward push of the operation member 34 from the restored level to the pushed level causes corresponding downward movement of the movable member 41, the cutter 43 integrally formed thereon, and the driver 44. At this time, the pin-like driver 44 moves downward along the first groove portion 13a of the feed groove 13 to move over the projection 13c provided at the intermediate portion of the first groove portion. When the pushing force applied to the operation member 34 is relieved, the operation member 34 and the movable member 41 move upward to the restored level by the elastic restoring force of the paired leaf springs 46. At this time, the pin-like driver 44, initially moving upward along the first groove portion 13a, is guided from the first groove portion 13a to the second groove portion 13b by the projection 13d and then moves over the projection 13d to be received in the adjacent first groove portion 13a.

With the sensor feeder described above, a sensor can be taken out from a sensor cartridge as follows.

First, a sensor cartridge 1 is inserted into the cartridge insertion hole 32 of the cartridge mount portion 30 of a sensor feeder 3 from one side thereof. By pushing the operation member 34 plural times, a feed mechanism, which is provided by the engagement of the feed grooves 13 formed on the rear surface 10d of the cartridge body 10 with the pin-like driver 44 movable vertically together with the movable member 41, operates to advance the cartridge 1 in a predetermined direction by the number of steps corresponding to the number of pushes.

Figure 11:
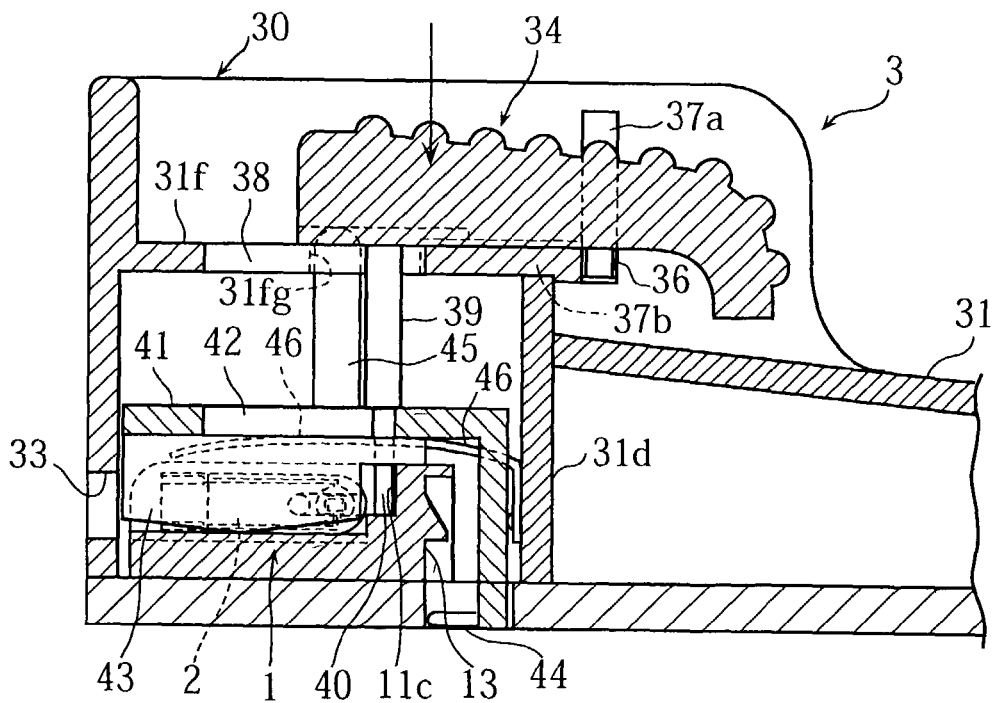
FIG. 11 is a sectional view taken along lines X-X in FIG. 9, showing the operation member at the retreated position on the pushed level.
Figure 12:
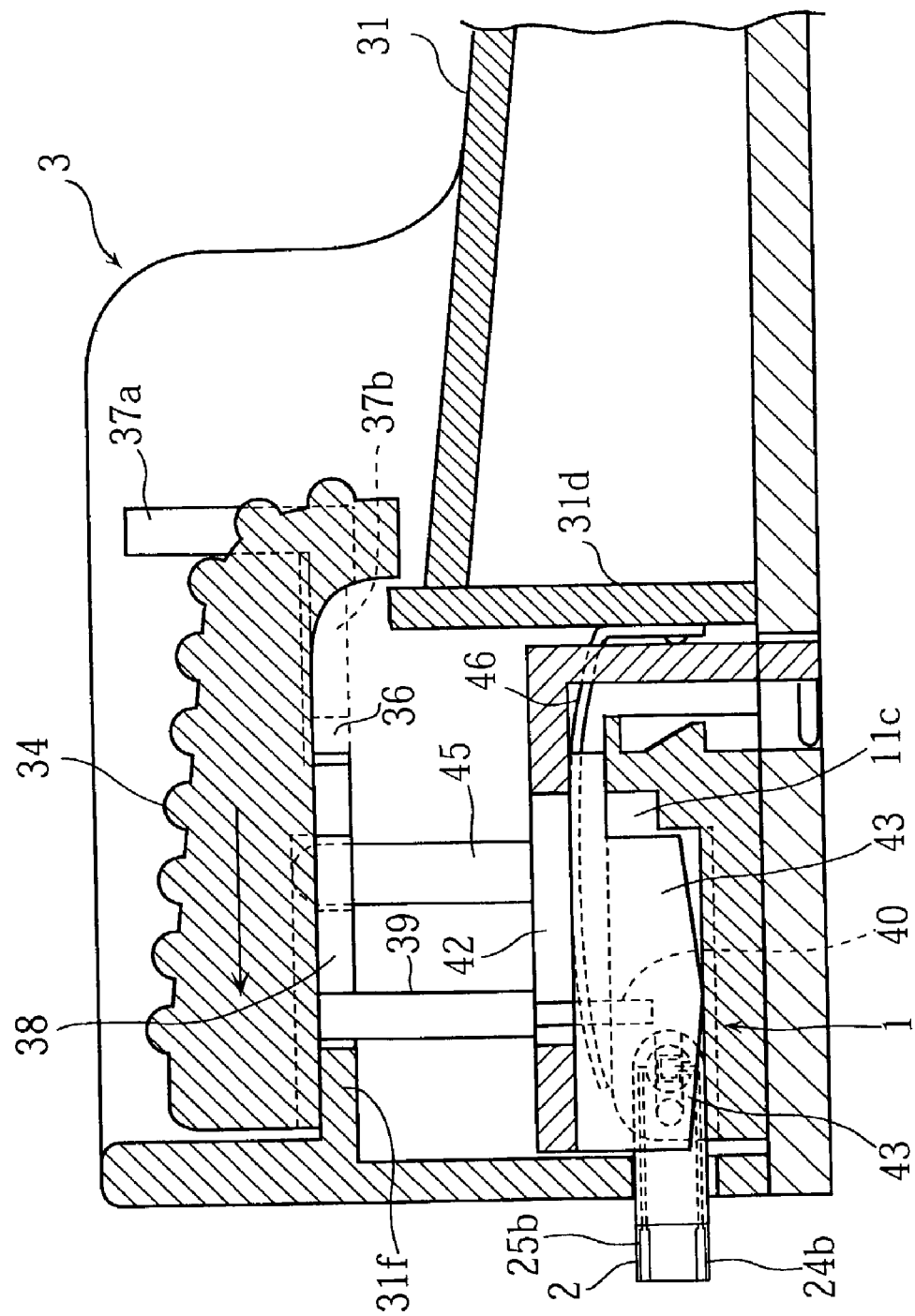
FIG. 12 is a sectional view taken along lines X-X in FIG. 9, showing the operation member at the advanced position on the pushed level.

As shown in FIG. 11, to take out the sensor 2 accommodated in the sensor retaining groove 11 of the sensor cartridge 1, the user pushes down the operation member 34, which is biased upward by the paired leaf springs 46, while holding the grip portion 31. At this time, the guide projection 36 at the side surface of the operation member 34 slides along the vertically-extending first portion 37a of each guide groove 37. Subsequently, as shown in FIG. 12, the operation member 34 is slid toward the front of the apparatus. At this time, the guide projection 36 slides along the horizontally-extending second portion 37b of the guide groove 37. As long as the guide projection 36 is located in the second portion 37b of the guide groove 37, the operation member 34 cannot return to the restored position, thereby keeping the pushed state.

As shown in FIG. 11, when the operation member 34 is depressed, the cutter 43 moves correspondingly to enter the cutter receiving portion 11b of the sensor retaining groove 11 of the sensor cartridge 1. At this time, the cutter 43 breaks the sheet-like sealing member 12 sealing the upper opening and the front opening of the sensor retaining groove 11. At the same time, the push on the operation member 34 cause the pusher 40 on the operation member 34 to break the sealing member 12 for entry into the pusher receiving portion 11c of the sensor retaining groove 11. The pusher receiving portion 11c is located adjacent to and held in communication with the sensor accommodating portion 11a on the rear side of the cartridge. Therefore, when the operation member 34 is slid forward as shown in FIG. 12, the pusher 40 moves from the pusher receiving portion 11c to enter the sensor accommodating portion 11a to push the sensor 2 forward. As a result, part of the sensor 2 passes through the front opening of the sensor retaining groove 11 to project out through the sensor eject hole 33 of the front wall 31a facing the opening. In the case where the sensor 2 is loaded in the sensor retaining groove 11 with terminals 24b, 25b located on the front side of the apparatus, the above-described operation makes the terminals 24b, 25b of the sensor 2 project outward through the sensor eject hole 33. In this state, the user inserts the portion provided with the terminals 24b, 25b of the sensor 2 into a predetermined portion of a measuring instrument, thereby performing intended measurement such as the blood glucose level measurement without directly touching the sensor 2 with fingers.

When the operation member 34 is returned from the advanced position to the retreated position, the operation member 34 returns from the pushed level to the restored level due to the biasing force of the paired leaf springs 46. At this time, as described with reference to FIG. 4, the sensor cartridge 1 advances in the predetermined direction by the pitch L by the feed mechanism consisting of the feed grooves 13 and the pin-like driver 44. In this embodiment, the sensor retaining grooves 11 are also arranged at the pitch L. Therefore, when the sensor cartridge 1 is advanced in the predetermined direction by the pitch L, another sensor retaining groove 11 which is still sealed by the sealing member 12 comes directly under the cutter 4 provided at the operation member 34. Thus, the feeder is ready for taking out the next sensor 2.

In this way, with the sensor feeder 3 having the above-described structure, a user, or a patient can take out a sensor 2 properly from each sensor retaining groove of the sensor cartridge 1 and mount the sensor to a measuring instrument by a simple operation without directly touching the sensor. At this time, since only a relatively small mechanical load is exerted on the sensor 2, the sensor itself is not required to have a considerably large rigidity. Therefore, no inconvenience is caused even if a sensor is further reduced in size as required.

Figure 13:
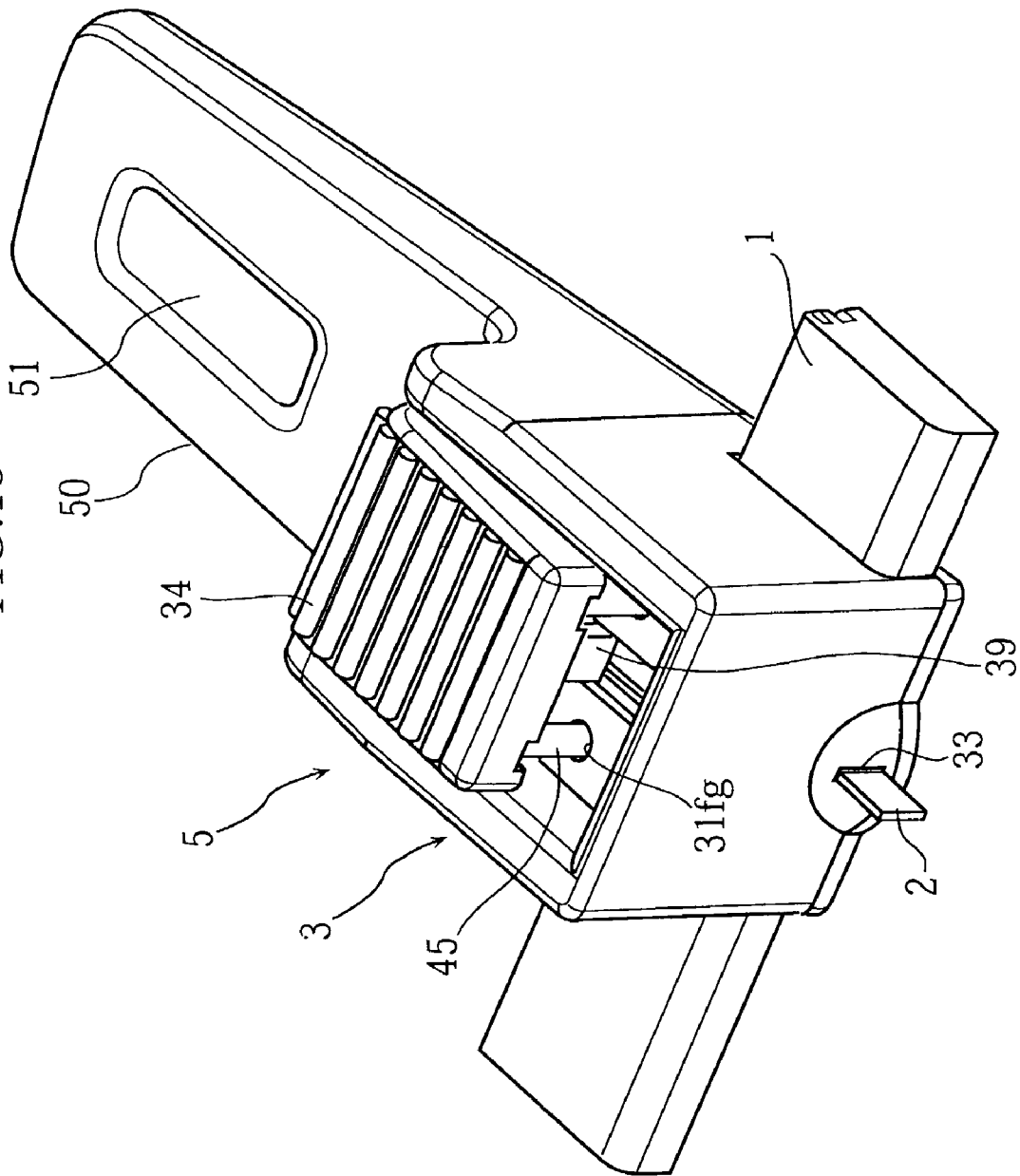
FIG. 13 is a perspective view showing an example of measuring instrument according to the present invention.
Figure 14:
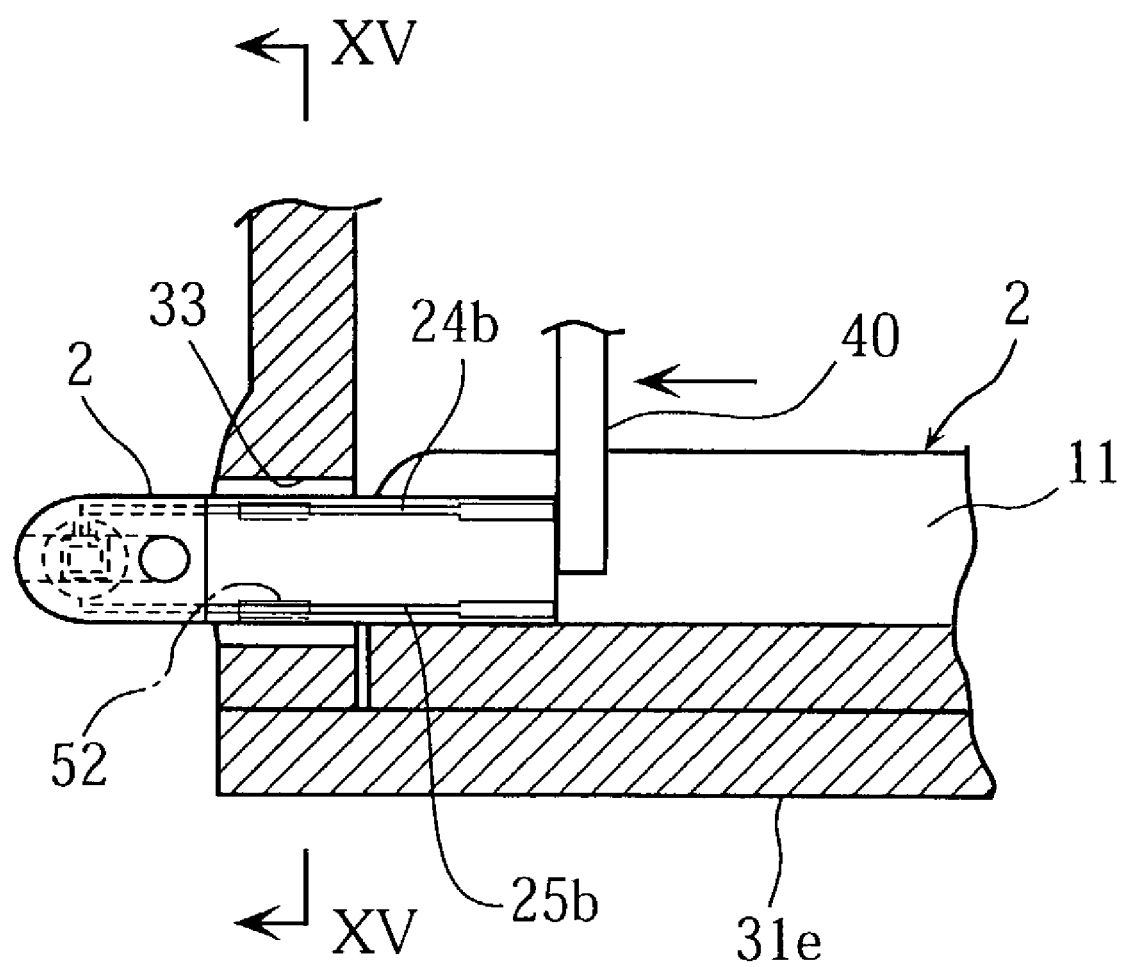
FIG. 14 is an enlarged sectional view illustrating the portions around the sensor eject hole of the measuring instrument of FIG. 13.
Figure 15:
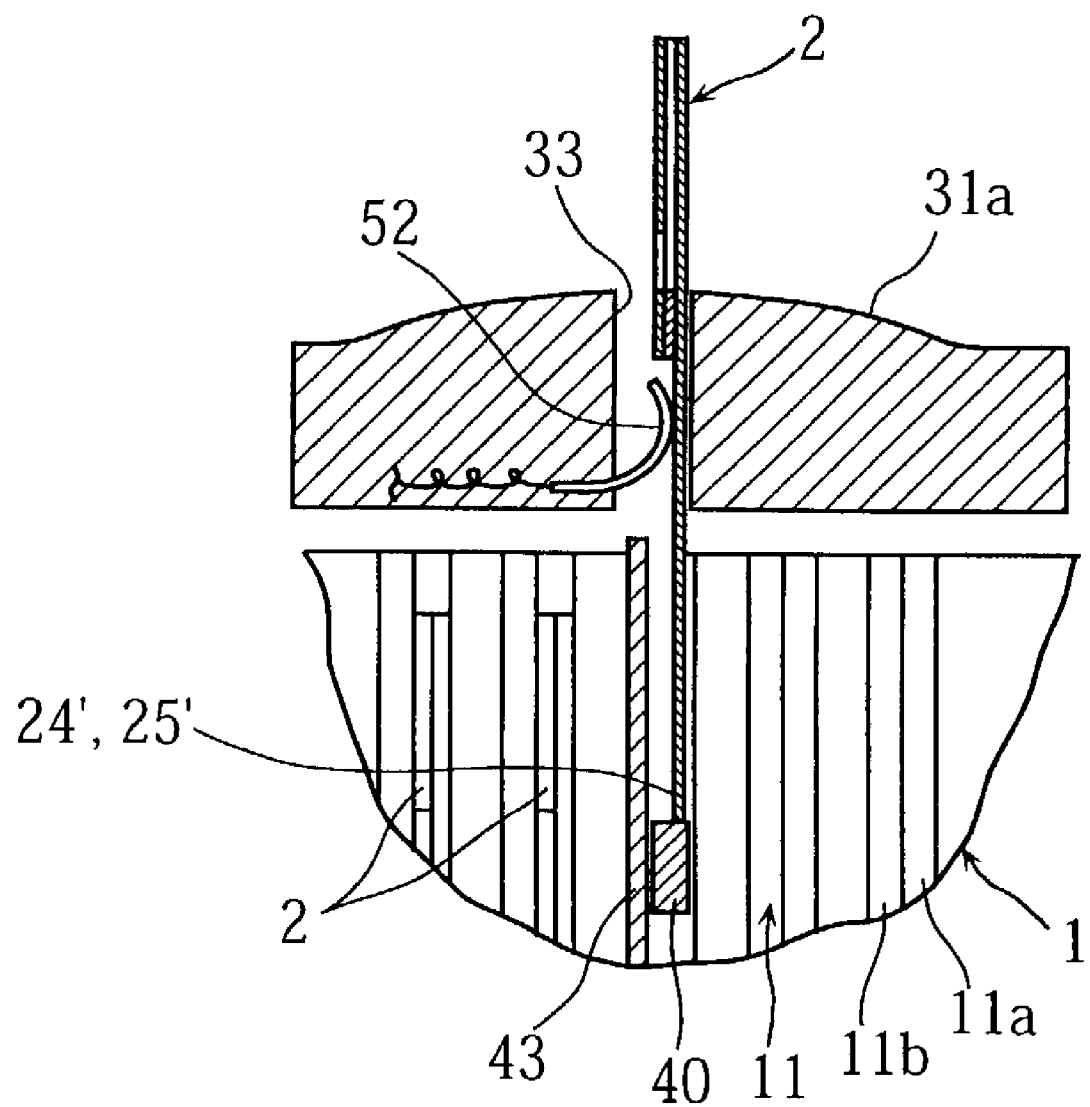
FIG. 15 is a sectional view taken along lines XV-XV in FIG. 14.

FIGS. 13 through 15 illustrate a measuring instrument 5 according to a third aspect of the present invention.

The measuring instrument 5 includes a main body 50 for the measuring instrument 5, and a sensor feeder 3 which is the second aspect of the present invention described above. The main body 50 is provided at the grip portion of the sensor feeder 3. The main body 50 has an obverse surface provided with a display 51 such as an LCD. The display 51 indicates the results of measurement performed using a sensor.

The sensor feeder 3 built in the measuring instrument 5 has a structure which is similar to that described above with reference to FIGS. 7-12, but further has structural features described below. As shown in FIG. 14, in the measuring instrument 5, each sensor 2 is loaded in the sensor cartridge 1 so that the terminals 24b, 25b are positioned on the rear side of the instrument.

As clearly shown in FIGS. 14 and 15, the measuring instrument includes terminals 52 provided in the sensor eject hole 33 at the front wall 31a of the cartridge mount portion 30 for electrical contact with the terminals 24b, 25b of the sensor 2 when the sensor projects out from the cartridge 1. The spacer plate 21 and the cover plate 23 may be made relatively short for ensuring contact between the terminals 24b, 25b of the sensor 2 and the terminals 52 of the instrument.

Since the other portions of the sensor feeder 3 are structurally similar to those described before, the detailed description thereof is omitted.

For measuring body fluid, the sensor 2 in the sensor cartridge 1 is pushed forward by pushing down the operation member 34 and sliding it forward. At this time, the tip end of the sensor 2 projects through the sensor eject hole 33 at the front wall 31a of the instrument as shown in FIG. 13, whereas the terminals 24b, 25b at the base end of the sensor 2 are brought into electric contact with the terminals 52 on the instrument side as shown in FIG. 15.

The user or the patient brings blood, which is drawn out onto the skin using e.g. a lancet, into contact with the analyte applying portion at the tip end of the sensor 2. Part of the blood is introduced into the body fluid path of the sensor 2 by capillary action. In the sensor, the reaction reagent dissolves in blood to cause enzyme reaction and electrochemical reaction, thereby generating an anode current at the operative electrode. The anode current passes through the terminals 52 on the side of the measuring instrument into a circuit in the measuring instrument 5. The measurement results such as the blood sugar level determined using a predetermined calibration curve is displayed at the display 51.

When the measurement finishes, the sensor 2 is pulled out for disposal and the operation member 34 is returned to the restored level. At this time, the sensor cartridge 1 is advanced stepwise by the feed mechanism to be ready for the next measurement.

In this way, with the measuring instrument 5 according to the third embodiment of the present invention, intended body fluid measurement can be performed without touching the sensor.

The present invention is not limited to the above-described embodiments. The configuration of the sensor retaining grooves may be modified appropriately in accordance with the given sensors. Further, the feed grooves provided at the rear surface of the sensor cartridge body may be configured otherwise as long as they can advance the cartridge step by step correspondingly to the vertical movement of the pin-like driver of the movable member.

The invention claimed is:

1. A sensor cartridge attached in use to a main body of a sensor feeder, the cartridge comprising:
   a cartridge body and a sealing member;
   the cartridge body including an upper surface, a front surface connected to the upper surface, and a plurality of sensor retaining grooves, each of the sensor retaining grooves including an upwardly directed first opening formed at the upper surface and a forwardly directed second opening formed at the front surface for communication with the first opening, the sealing member closing the first opening and the second opening with a sensor loaded in the sensor retaining groove.

2. The sensor cartridge according to claim 1, wherein the sensor retaining groove includes a sensor accommodating portion for accommodating the sensor, and a pusher receiving portion for receiving a pusher contained in the main body of the sensor feeder, the sensor accommodating portion communicating with the first opening and the second opening, the pusher receiving portion communicating with the first opening while being connected to the sensor receiving portion at a location opposite to the second opening.

3. The sensor cartridge according to claim 1, wherein the sensor retaining groove includes a sensor accommodating portion for accommodating the sensor, and a cutter receiving portion for receiving a cutter contained in the main body of the sensor feeder, the sensor accommodating portion and the cutter receiving portion communicating with the first opening and the second opening while being connected to each other.

4. The sensor cartridge according to claim 3, wherein the cutter receiving portion is deeper than the sensor accommodating portion in thicknesswise of the sensor cartridge.

5. The sensor cartridge according to claim 1, wherein the front surface is connected to the upper surface via a rounded portion.

6. The sensor cartridge according to claim 1, further comprising a rear surface opposite to the front surface, the rear surface being formed with feed grooves for engaging a pin included in the main body of the sensor feeder and for advancing the sensor cartridge by a predetermined pitch in response to one reciprocal movement of the pin.

7. The sensor cartridge according to claim 6, wherein each of the feed grooves includes a first groove portion extending in thicknesswise of the sensor cartridge and a second groove portion extending between an intermediate portion of the first groove portion and an upper end of an adjacent first groove portion.

8. The sensor cartridge according to claim 7, wherein the intermediate portion of the first groove portion is provided with a projection for guiding the pin moving upward within the first groove portion toward the second groove portion.

9. The sensor cartridge according to claim 7, wherein the second groove portion is provided with a projection for preventing the pin from entering the second groove portion from the upper end of the first groove portion.

10. The sensor cartridge according to claim 6, wherein the plurality of sensor retaining grooves are arranged at said predetermined pitch.

11. A sensor feeder comprising:
a sensor cartridge including a cartridge body and a sealing member for accommodating a plurality of sensors; and
a pusher movable vertically and back and forth for pushing one of the plurality of sensors;
the cartridge body including an upper surface, a front surface connected thereto, and a plurality of sensor retaining grooves, each of the sensor retaining grooves including an upwardly directed first opening formed at the upper surface and a forwardly directed second opening formed at the front surface for communication with the first opening, the sealing member closing the first opening and the second opening with a sensor loaded in the sensor retaining groove;
the sensor retaining groove including a sensor accommodating portion for accommodating the sensor, and a pusher receiving portion for receiving the pusher, the sensor accommodating portion communicating with the first opening and the second opening, the pusher receiving portion communicating with the first opening while being connected to the sensor receiving portion at a location opposite to the second opening.

12. The sensor feeder according to claim 11, further comprising a cutter for breaking the seating member, the sensor retaining groove including a cutter receiving portion for receiving the cutter, the cutter receiving portion communicating with the first opening and the second opening while being connected to the sensor accommodating portion.

13. The sensor feeder according to claim 12, further comprising a pin, the cartridge body including a rear surface opposite to the front surface, the rear surface being formed with feed grooves for engaging the pin and for advancing the sensor cartridge by a predetermined pitch in response to one reciprocal movement of the pin.

14. The sensor feeder according to claim 13, further comprising an operation member which is movable vertically and back and forth, the pusher, the cutter and the pin being movable vertically in response to the vertical movement of the operation member, the pusher being movable back and forth in response to the back-and-forth movement of the operation member.

15. The sensor feeder according to claim 14, further comprising a spring for biasing the operation member upward.

16. A sensor cartridge comprising:
a cartridge body having an upper surface and a plurality of sensor retaining grooves each having an upwardly directed opening formed at the upper surface; and
a sealing member for closing the opening;
each of the sensor retaining grooves including a sensor accommodating portion for accommodating the sensor, and a cutter receiving portion for receiving a cutter for breaking the sealing member without interfering with the sensor, the sensor accommodating portion and the cutter receiving portion communicating with the opening while being connected to each other, the sensor accommodating portion and the cutter receiving portion being offset from each other widthwise relative to the sensor retaining groove.

* * * * *